United States Patent
Schmieding

(10) Patent No.: US 6,823,871 B2
(45) Date of Patent: Nov. 30, 2004

(54) ALLOGRAFT BONE OR SYNTHETIC WEDGES FOR OSTEOTOMY

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/872,100

(22) Filed: Jun. 1, 2001

(65) Prior Publication Data

US 2002/0010513 A1 Jan. 24, 2002

Related U.S. Application Data

(60) Provisional application No. 60/208,308, filed on Jun. 1, 2000.

(51) Int. Cl.[7] .................................................. A61F 5/00
(52) U.S. Cl. ......................................... 128/898; 606/87
(58) Field of Search ............................ 128/898; 606/87, 606/88, 60, 72, 79, 86; 623/23.58, 23.61, 23.63, 16.11, 17.11, 17.16

(56) References Cited

U.S. PATENT DOCUMENTS

| | | | |
|---|---|---|---|
| 4,563,489 A | * | 1/1986 | Urist .......................... 623/915 |
| 5,620,448 A | | 4/1997 | Puddu ......................... 606/87 |
| 5,749,875 A | | 5/1998 | Puddu ......................... 606/87 |
| 6,086,593 A | * | 7/2000 | Bonutti ....................... 606/87 |
| 6,200,347 B1 | * | 3/2001 | Anderson et al. ......... 623/16.11 |
| 6,203,546 B1 | * | 3/2001 | MacMahon .................. 606/87 |
| 6,287,308 B1 | * | 9/2001 | Betz et al. ................... 606/61 |

* cited by examiner

Primary Examiner—Danton D. DeMille
(74) Attorney, Agent, or Firm—Dickstein Shapiro Morin & Oshinksy, LLP

(57) ABSTRACT

Methods of performing opening wedge osteotomies are disclosed in which healing of the osteotomy defect is enhanced by packing the opening with pre-packaged, wedge-shaped bone grafts. The bone wedges are provided in sets of three: two larger outer pieces and a smaller inner piece that fits behind a bone plate. The wedge pieces are made of allograft bone or synthetic bone material. Outer surfaces of the two larger pieces preferably are cortical bone or cortical bone-like material.

16 Claims, 10 Drawing Sheets

ALLOGRAFT BONE OR SYNTHETIC WEDGES FOR OSTEOTOMY

This application claims the benefit of U.S. Provisional Application Ser. No. 60/208,308, filed Jun. 1, 2000.

BACKGROUND OF THE INVENTION

1. Field of the Invention

The present invention relates to systems and methods for performing opening wedge osteotomies. More specifically, the present invention relates to opening wedge osteotomy systems, and pre-packaged bone graft sets for packing into an osteotomy defect to promote healing, for performing opening wedge osteotomies.

2. Description of the Related Art

Treatment of pain and/or instability associated with lower extremity misalignment may require surgical interventions that include osteotomy. High tibial osteotomies (HTO) are indicated by early, medial joint-space narrowing, by early arthritis in patients who have had previous medial meniscectomy, or following rupture of the anterior cruciate ligament (ACL) in patients with pre-existing varus deformity, for example.

Opening wedge osteotomy procedures are disclosed in U.S. Pat. No. 5,620,448 issued Apr. 15, 1997, and U.S. Pat. No. 5,749,875 issued May 12, 1998, the disclosures of which are incorporated herein by reference.

The known procedures could benefit from advancements in techniques, instrumentation, and materials to make the results more reproducible and reliable.

SUMMARY OF THE INVENTION

The present invention provides an improved system for performing the opening wedge osteotomy procedure. The system includes pre-packaged bone graft wedges for packing the osteotomy site. In addition, advanced instrumentation for performing the surgery is provided.

A preferred method of correcting a deformity in a patient by performing an osteotomy in a bone at an osteotomy site uses a bone plate having a projection that is inserted into the osteotomy defect, as described more fully below. Wedges of bone graft material are packed into the defect opening to promote healing and reliability of the repair.

The bone graft material preferably is provided in a three piece, prepackaged set. The bone graft material preferably is either allograft bone, or synthetic bone. A preferred synthetic bone material is made up of either tricalcium phosphate (TCP) or hydroxyapatite (HA), combined with a biodegradable polymer, preferably a polylactide, such as PLA.

The three-piece set includes a smaller, inner piece, and two larger outer pieces. The inner piece is made up of cancellous bone or a synthetic substitute. The outer pieces have inner portions made of the same material as the smaller inner piece, and also have an outer surface that is mostly cortical bone or a synthetic substitute. When using allograft bone, the harvested bone is freeze dried. The prepackaged pieces can by trimmed to shape for the osteotomy by the surgeon.

Other features and advantages of the present invention will become apparent from the following description of the invention which refers to the accompanying drawings.

DETAILED DESCRIPTION OF THE PREFERRED EMBODIMENTS

Figure 1:
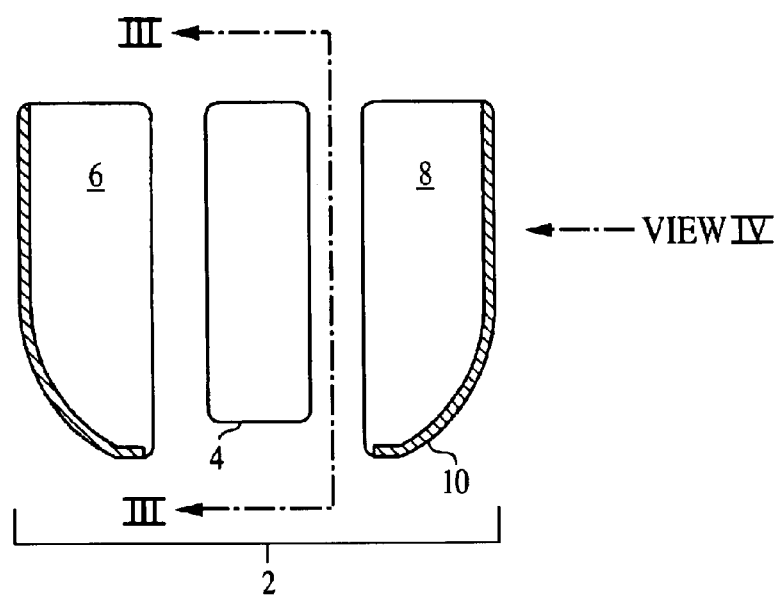
FIG. 1 is a plan view of a three-piece opening wedge osteotomy bone graft set according to the present invention.
Figure 2:
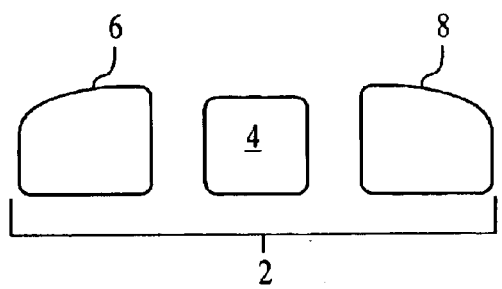
FIG. 2 is an elevation view of the three-piece opening wedge osteotomy bone graft set shown in FIG. 1.
Figure 3:
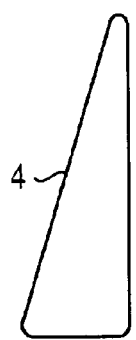
FIG. 3 is a side view of a smaller wedge piece from the graft set of FIGS. 1 and 2.
Figure 4:
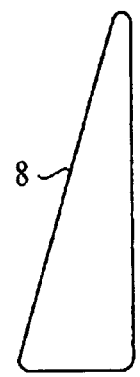
FIG. 4 is a side view of a larger wedge piece from the graft set of FIGS. 1 and 2.

Referring initially to FIGS. 1 and 2, a set 2 of allograft bone wedges for insertion into an opening wedge osteotomy is shown. Wedge set 2 is made up of three pieces: a smaller inner wedge 4 flanked by two larger outer wedges 6 and 8. Inner wedge 4 is made entirely of allograft cancellous bone or a synthetic cancellous bone, and is sized to fit behind a bone plate as described more fully below. Outer wedges 6, 8 are made of allograft or synthetic cancellous bone with rounded outside surfaces covered with an allograft or synthetic cortical bone 10 shell, as shown in FIG. 1. The outer shell 10 provides a replacement for the gap in the cortical shell created by the osteotomy procedure. Preferably at least about 80% of the outer surfaces of outer wedges 6, 8 is cortical bone. As seen in FIGS. 3 and 4, the wedge shape is formed linearly to fit into the osteotomy defect, as described further below.

Figure 5:
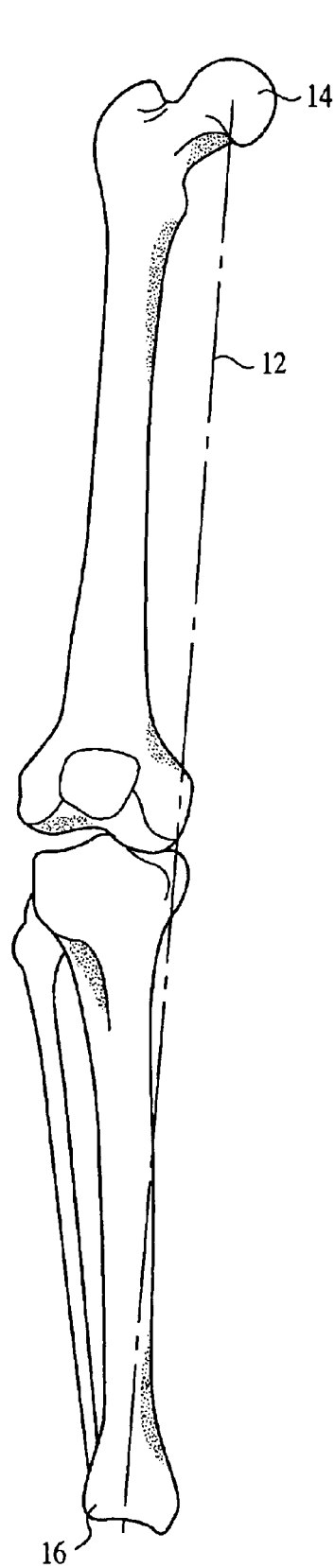
FIG. 5 is a schematic illustration of a step of determining a patient's mechanical axis according to the present invention.
Figure 6:
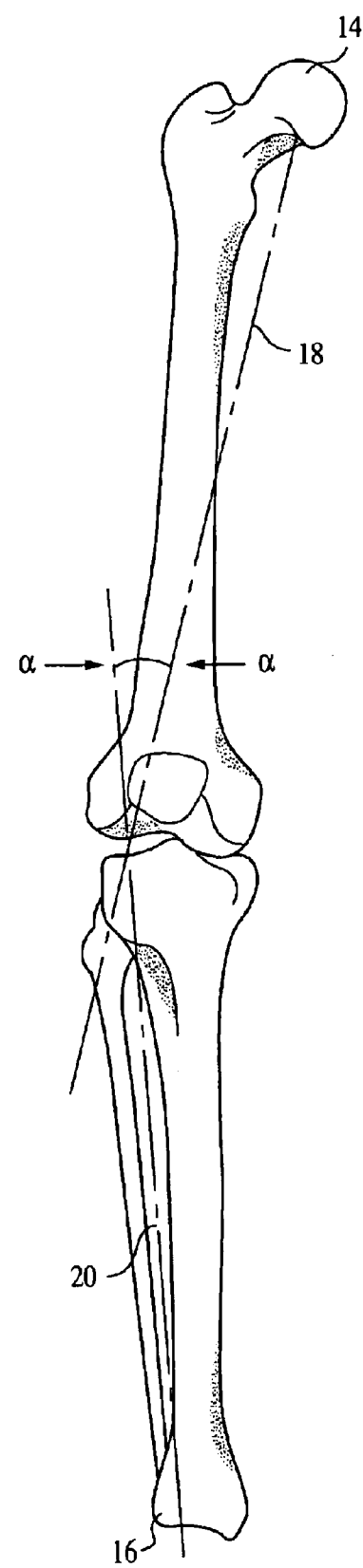
FIG. 6 is a schematic illustration of a step of determining a degree of correction required by an osteotomy patient.

Referring to FIG. 5, a preferred method of correcting a deformity in a patient begins by determining a degree of correction required to correct the deformity. Using a full-length standing radiograph of the patient, a line 12 is drawn from the center of a femoral head 14 to the center of a tibial-talar joint 16 to demonstrate the patient's mechanical axis. As shown in FIG. 6, a second line 18 is drawn from the center of the femoral head 14 to a point midway in the lateral knee joint. This point midway in the lateral knee joint preferably is located at 62.5% of the width of the proximal tibia. A third line 20 is drawn from the center of the tibial-talar joint 16 to the point midway in the lateral knee joint. Measuring the angle α formed by the intersection of the second and third lines determines the degree of correction required to return the patient's mechanical axis to the point midway in the lateral knee joint. For each degree of correction, approximately 1 mm of osteotomy opening is required. Prior to final fixation, the alignment will be verified by external examination using an alignment rod, and by fluoroscopy.

Prior to performing the osteotomy, a diagnostic arthroscopy is performed to verify the status of the articular cartilage and menisci. Any necessary debridement and resection is carried out. Focal defects in the articular surface can be addressed utilizing the techniques disclosed in U.S. Pat. No. 5,919,196 issued Jul. 6, 1999, assigned to the assignee of the present application.

Figure 7:
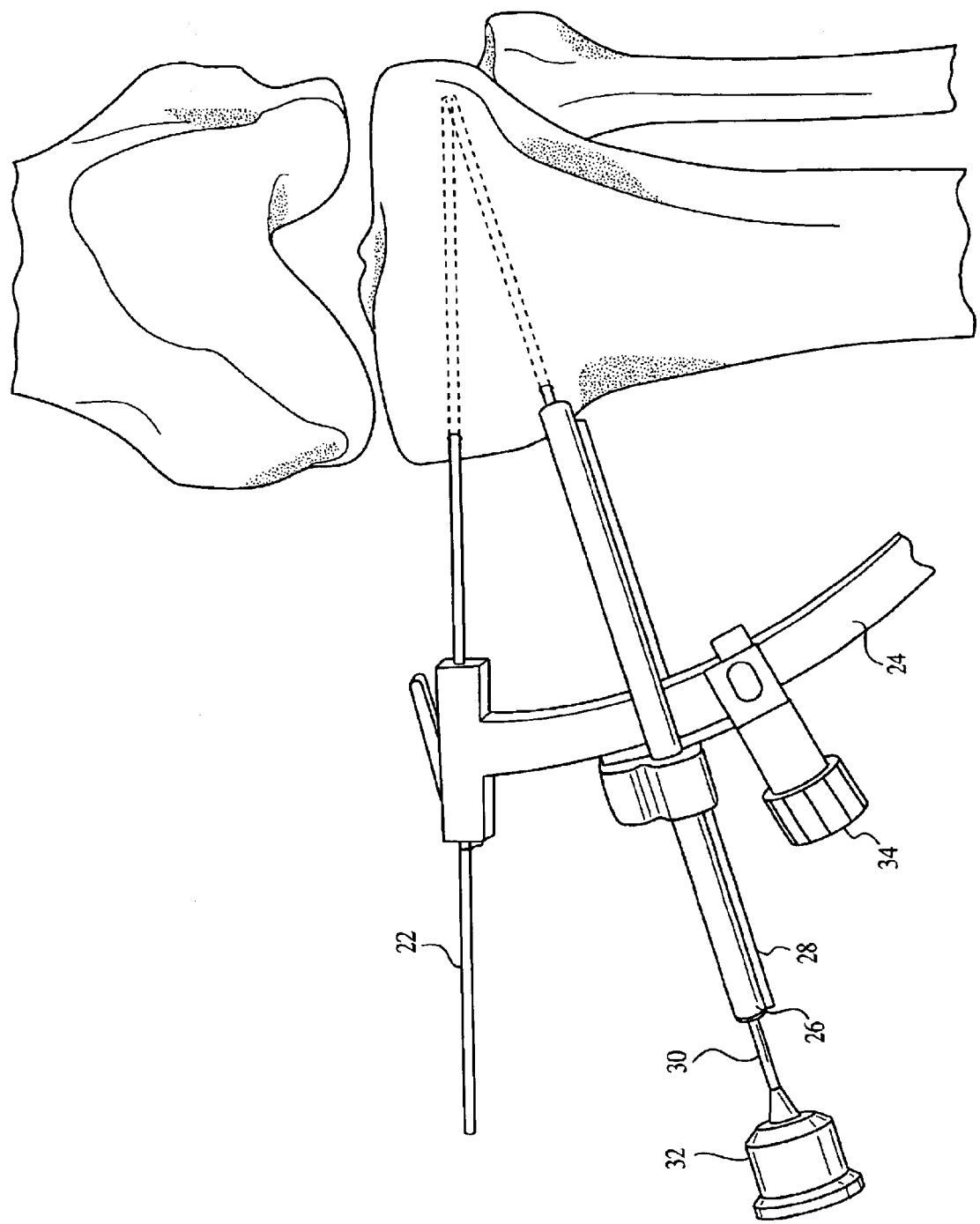
FIG. 7 illustrates steps of placing guide pins and a guide assembly according to the present invention.

After forming an appropriate incision, a 3.0 mm guide pin 22 is installed transversely into the bone about 1–2 cm below the joint line as shown in FIG. 7. Guide pin 22 preferably is installed medial to lateral, and does not penetrate the lateral side. Once guide pin 22 has been installed, a parallel guide assembly 24 is inserted onto guide pin. The guide assembly includes a parallel pair of drill guide sleeves 26 and 28 that are used to install a pair of 2.4 mm breakaway guide pins 30 into the bone using a pin driver 32. The parallel guide sleeves can be rotated to reproduce the existing AP slope of the tibial plateau. Using an adjustment knob 34, the angle of the guide can be adjusted so that pins 30 will enter the proximal tibia above the tibial tubercle. Adjustment knob 34 is tightened, and pins 30 are advanced into the bone to within about 1 cm of the lateral side. Once pins 30 are placed in an acceptable position, the parallel guide assembly 24 and transverse pin 22 are removed.

Figure 8:
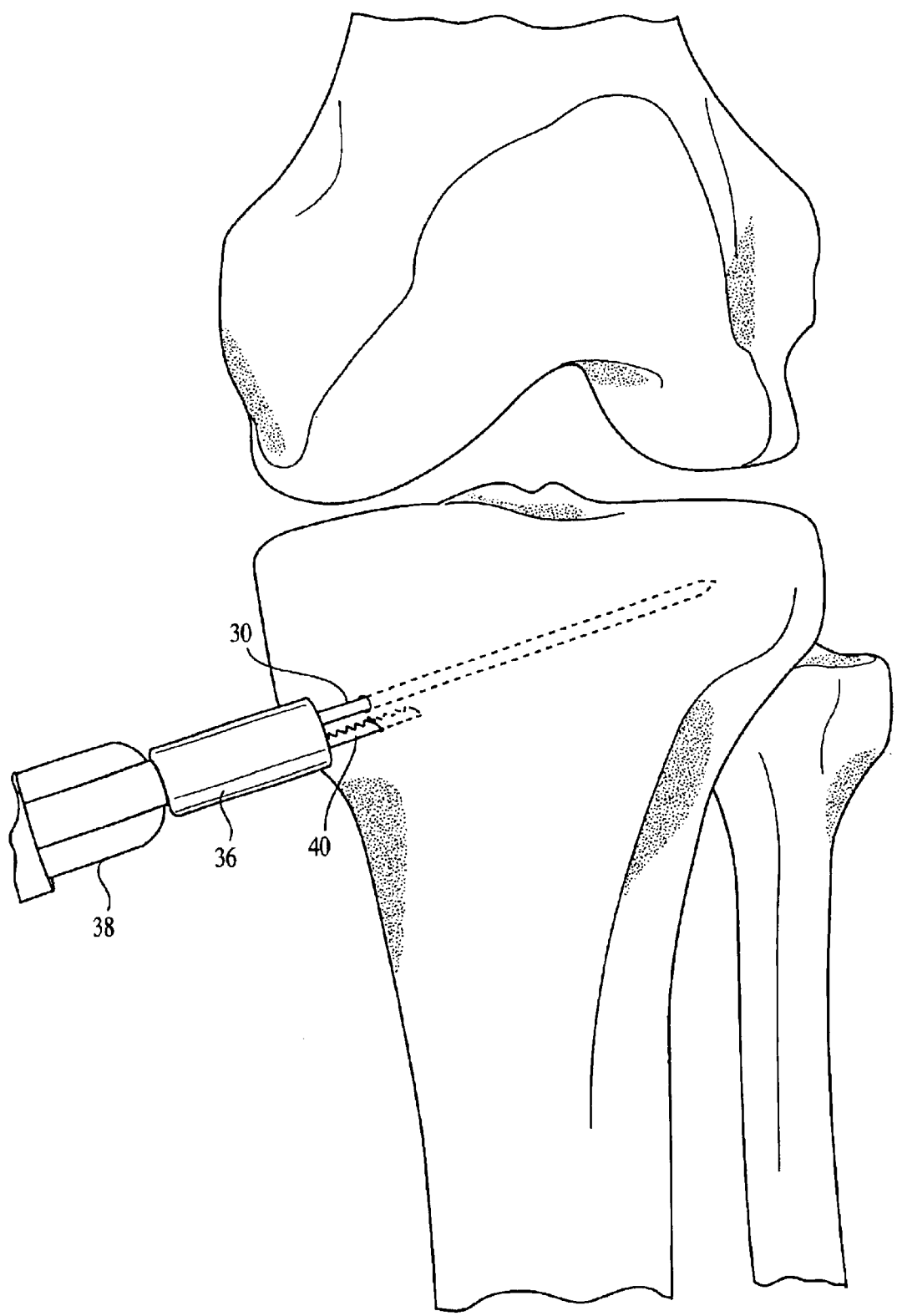
FIG. 8 illustrates a step of cutting an osteotomy resection using an oscillating saw according to the present invention.
Figure 9:
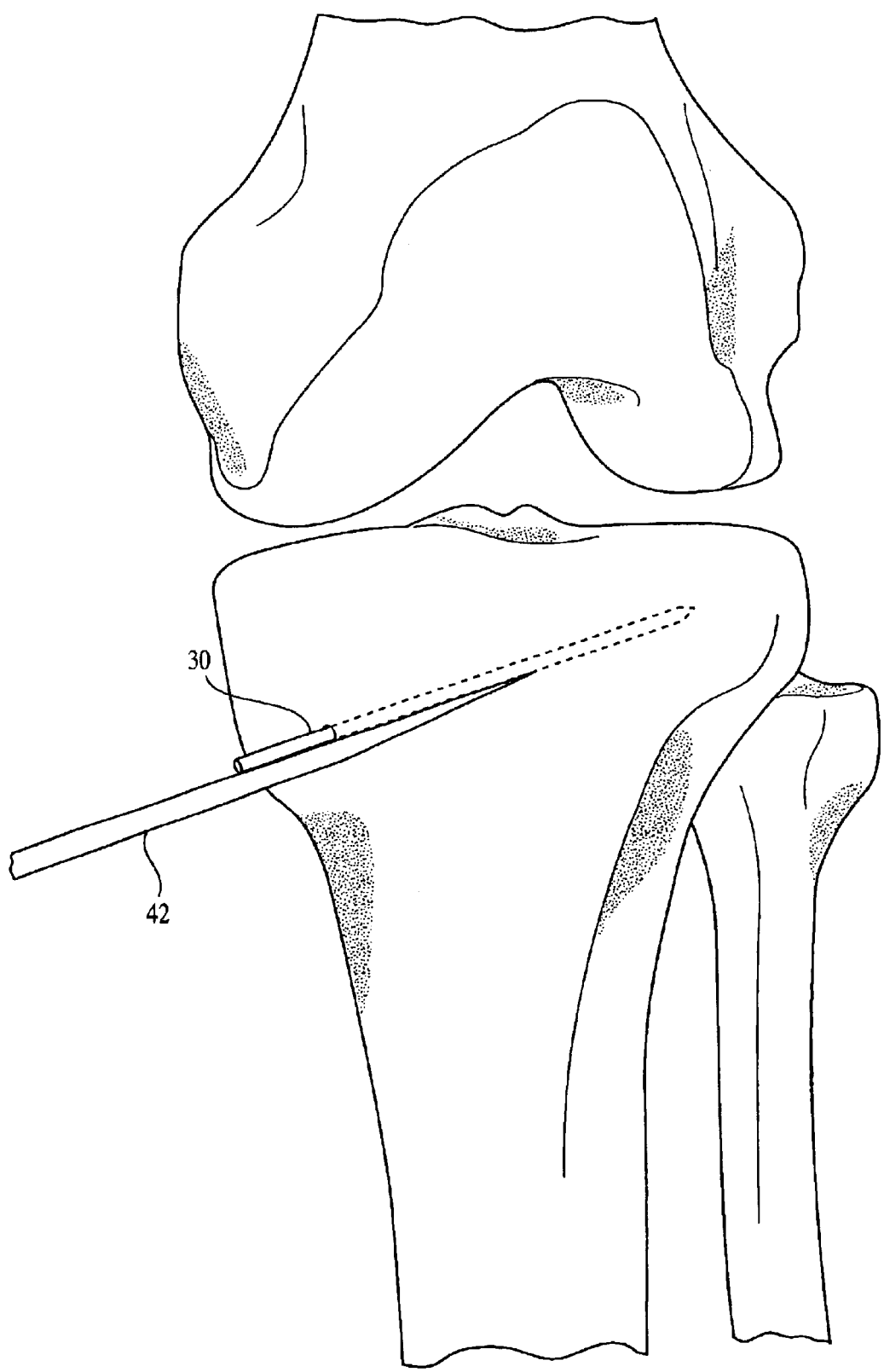
FIG. 9 illustrates a step of cutting an osteotomy resection using an osteotome according to the present invention.

Referring next to FIG. 8, the parallel guide assembly 24 is replaced on the guide pins 30 by a cutting guide 36. An oscillating saw 38 is used to begin the resectioning of the osteotomy. Cutting guide 36 provides a guide slot for saw blade 40 as it is advanced into the bone. Breakaway guide pins 30 have been broken off to accommodate saw 38. Referring to FIG. 9, pins 30 have been further shortened, and an osteotome 42 is advanced into the bone to complete the resection.

Figure 10:
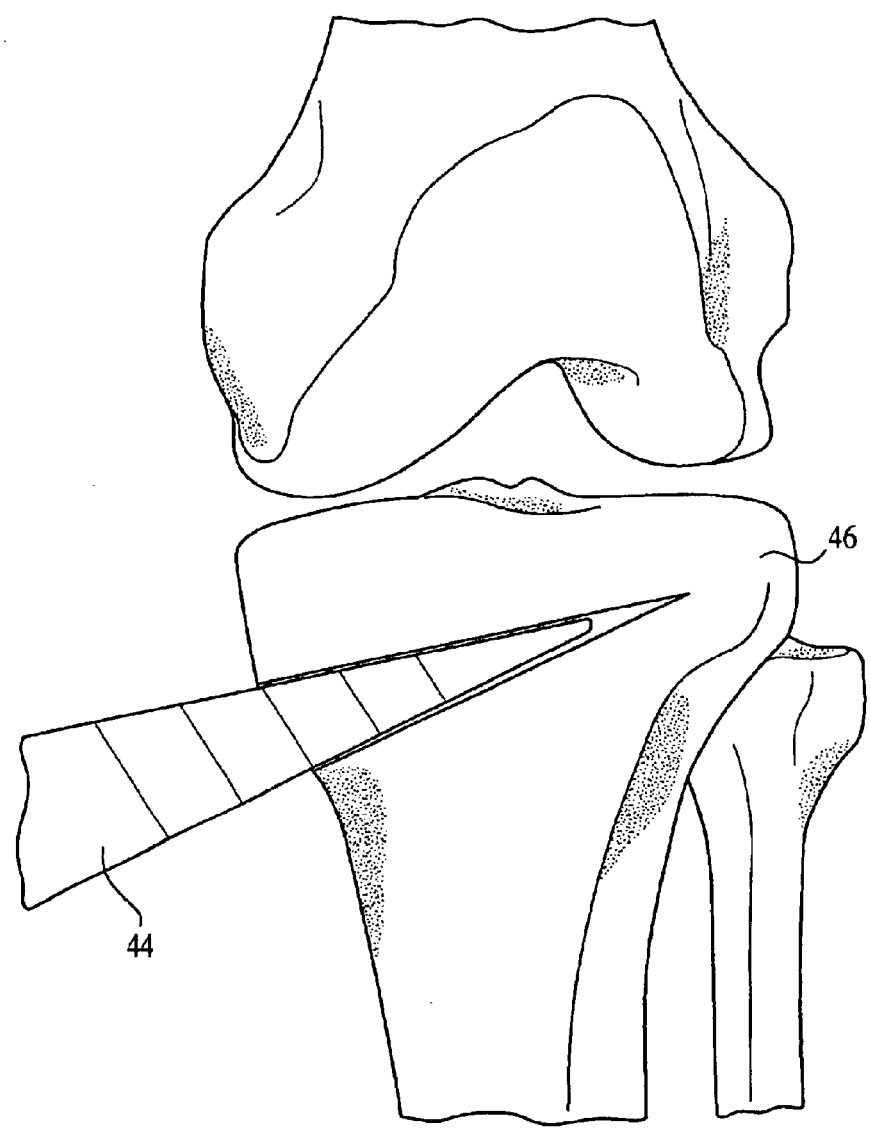
FIG. 10 illustrates a step of inserting a forked wedge opening tool to open the osteotomy according to the present invention.
Figure 11:
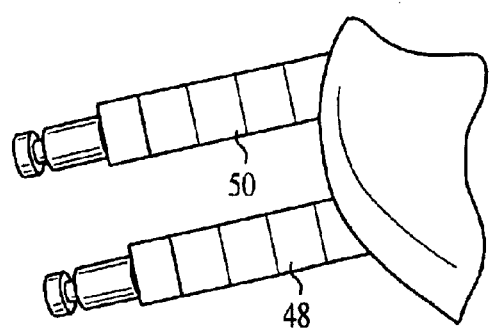
FIG. 11 is a plan view illustrating steps of removing a handle from the forked wedge opening tool, leaving the tines in place according to the present invention.

Referring to FIGS. 10 and 11, a forked wedge tool 44 is advanced into the resection. Using impact force, tool 44 is advanced carefully to allow plastic deformation of the bone hinge 46 as the resection is opened by the wedge tines 48 and 50. As shown in FIG. 11, the tines are calibrated to indicate the size of the opening being created as tool 44 is advanced. Once the desired angle of correction has been achieved, a handle of the forked wedge tool is removed, leaving tines 48 and 50 in place holding the osteotomy open as shown in FIG. 11. At this point, the smaller allograft wedge piece 4 can be packed in between the tines.

Figure 12:
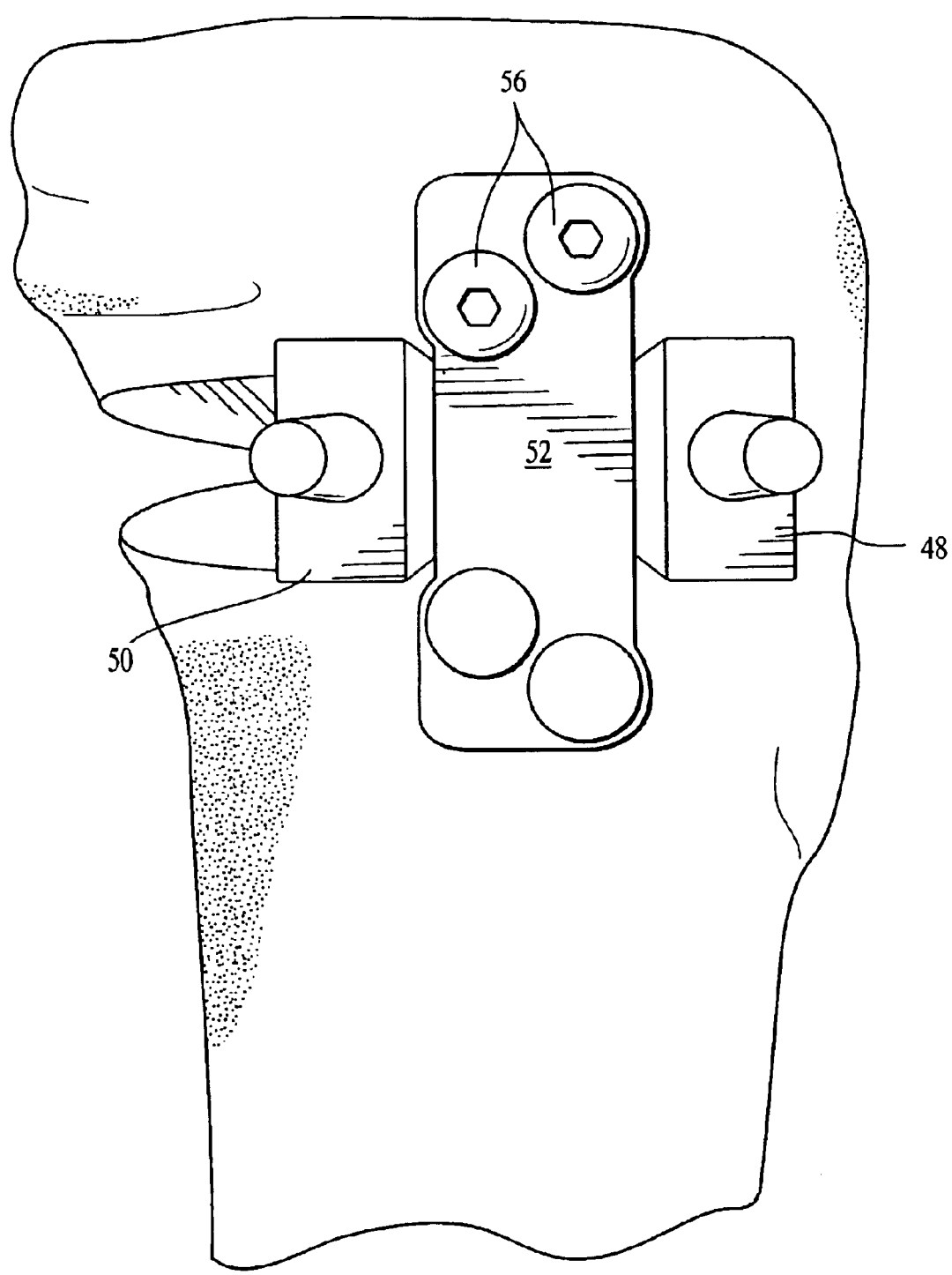
FIG. 12 illustrates the steps of installing a bone plate according to the present invention.
Figure 14:
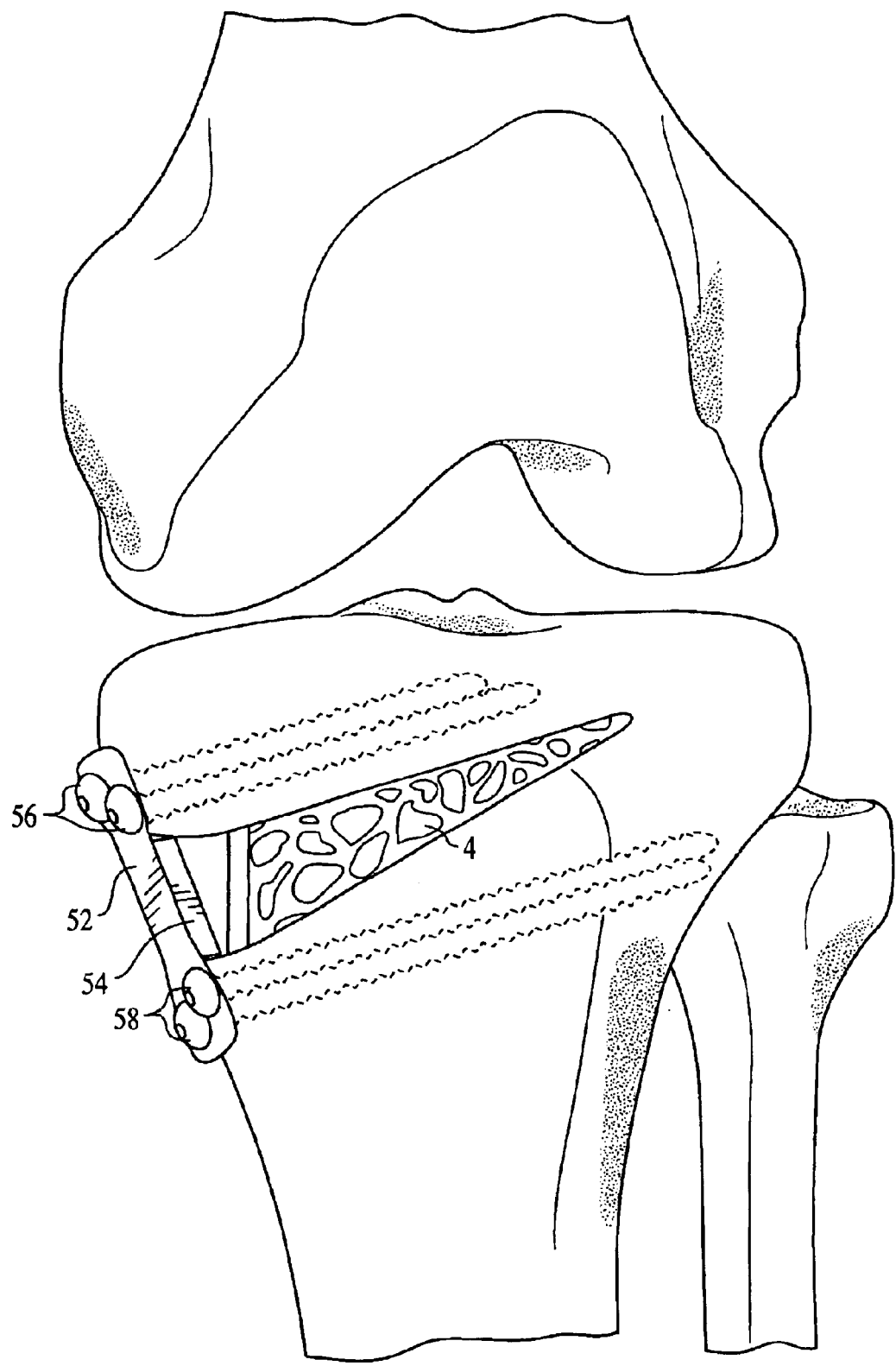
FIG. 14 illustrates the steps of packing the bone graft wedges of FIGS. 1–4 into the osteotomy according to the present invention.

Referring to FIG. 12, fixation of the osteotomy opening is provided by a bone plate 52 inserted between the tines so that a projection or "tooth" 54 (FIG. 14) on the bone plate sits within the osteotomy opening. The plate routinely sits just anterior to the medial collateral ligament. Two stainless steel 6.5 mm cancellous screws 56 are fixed proximally.

The plates are provided in various sizes to fit 5 mm, 7.5 mm, 9 mm, 10 mm, 11 mm, 12.5 mm, 15 mm and 17.5 mm corrections for example. Advantageously, the projection or "tooth" can be provided with a 5° slope to augment the physiologic 5° slope of the tibial plateau. The tooth of the sloped plate has a 2.5° slope superiorly and a 2.5° inferiorly, addin to a toal slope of 5°. In a medial osteotomy, the slope of the plate tooth can face posteriorly to add 5° of slop, or face anteriorly to subtract 5° of slope. With an ACL deficient knee, it is not advixed to add posterior slope. With a PCL deficient knee, it is advised to add posterior slope to promote improved knee function. The plate can be provided with a threaded hole or other means for accommodating a manipulating device for ease of plate handling by members of the surgical team.

Figure 13:
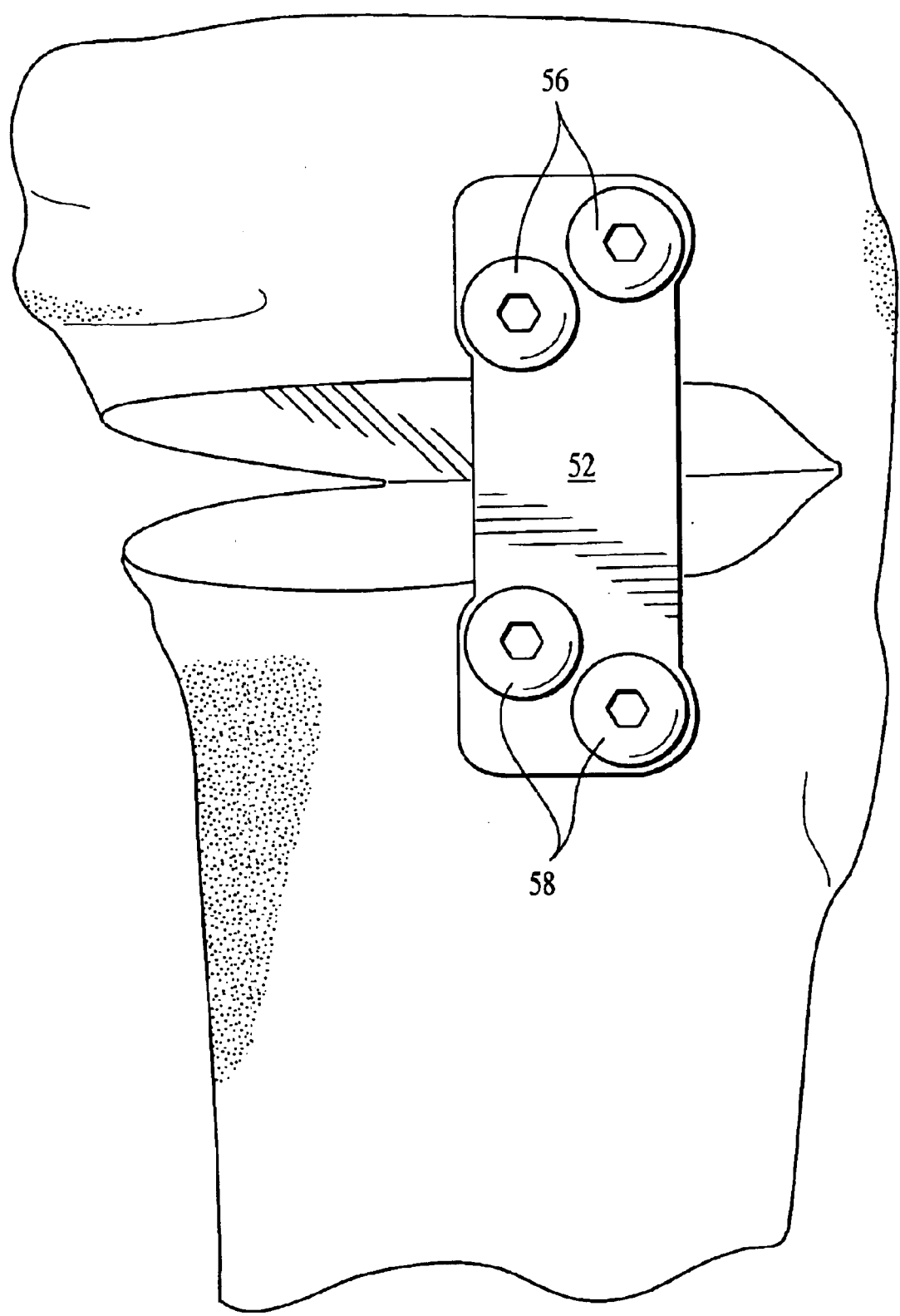
FIG. 13 illustrates the steps of removing the tines from the osteotomy once the bone plate is secured according to the present invention.

As shown in FIG. 13, fixation is completed distally using two 4.5 mm cortical screws 58. Tines 48 and 50 having been removed, larger bone graft wedges 6 and 8 are installed on either side of smaller wedge 4 shown in FIG. 14.

Figure 15:
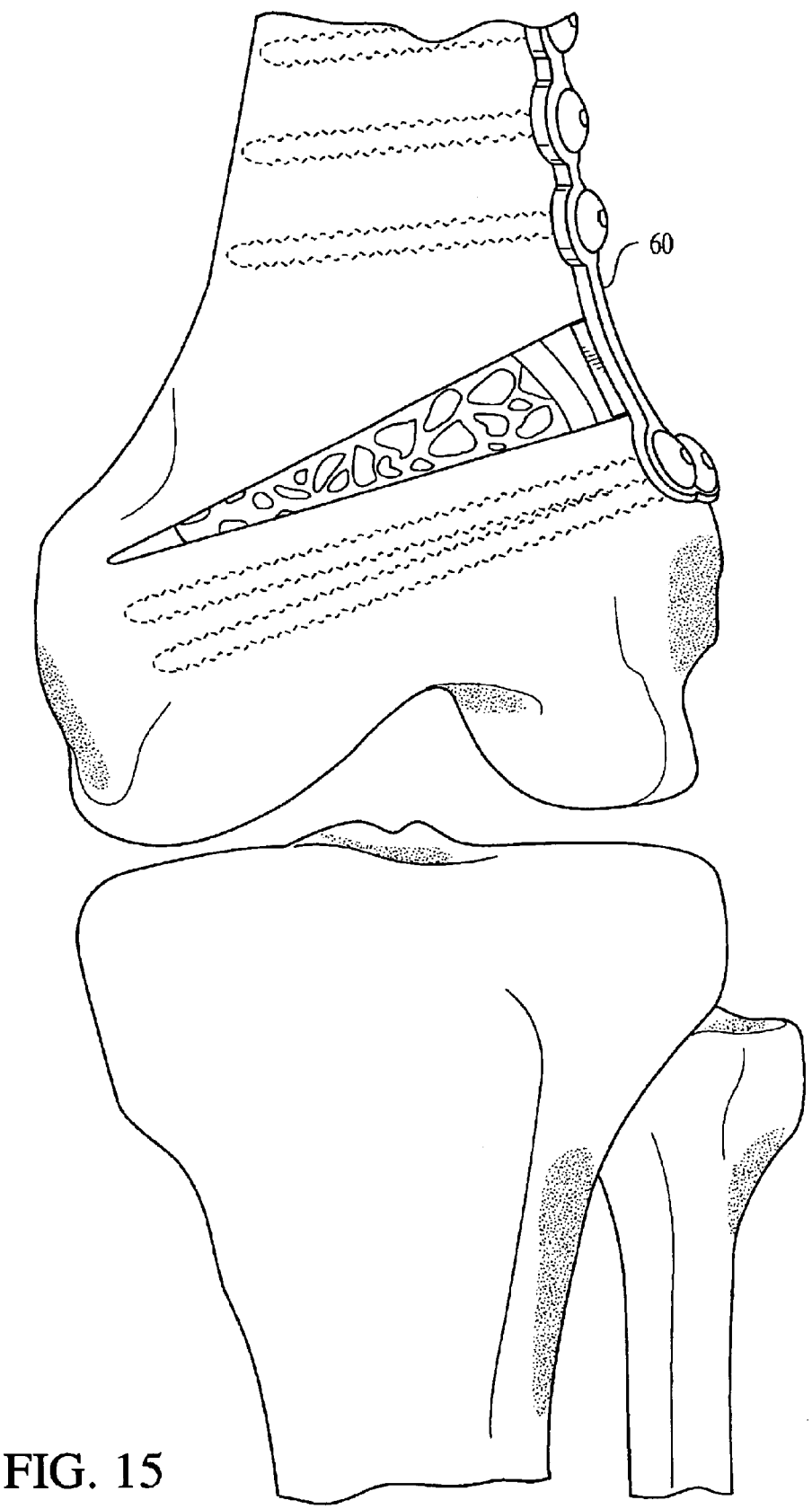
FIG. 15 illustrates an alternative method of performing a femoral osteotomy according to the present invention.

Although the method has been described above in connection with a medial femoral procedure, the invention is not so limited, and also is applicable, for example to a lateral tibial procedure as shown in FIG. 15. The procedure is modified, for example, by using a bone plate 60 that accommodates the bone curvature.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of correcting a deformity by performing an osteotomy in a bone at an osteotomy site using a bone plate, the method comprising the steps of:
   (a) resecting the bone from a first side of the bone to a second side of the bone so as to leave a bony hinge on the second side;
   (b) opening the resection to a height at which the deformity is corrected using an opening tool;
   (c) placing the bone plate in a location such that the bone plate spans the open resection;
   (d) removing the opening tool; and
   (e) packing the open resection with at least two individual pre-formed wedge shaped sections of material by inserting at least two individual, unconnected pre-formed wedge shaped sections into the open resection.

2. The method of claim 1, wherein the step of packing the resection includes the steps of inserting a smaller inner section of wedge shaped material behind the bone plate, and inserting two larger outer sections of wedge shaped material on either side of the smaller wedge section within the resection.

3. The method of claim 1, wherein the two wedge shaped sections of material have Outer surfaces formed of cortical bone.

4. The method of claim 2, wherein the step of inserting the smaller inner section takes place prior to placing the bone plate.

5. The method of claim 1, wherein the material comprises allograft bone.

6. The method of claim 1, wherein the material comprises synthetic bone.

7. The method of claim 6, wherein the synthetic bone comprises a biodegradable polylactide combined with a hydroxyapatite or tricalcium phosphate.

8. The method of claim 1, further comprising the step after opening the resection of removing a removable handle from the opening tool to provide access for the bone plate prior to the step of placing the bone plate.

9. A method of correcting a deformity by performing an osteotomy in a bone at an osteotomy site using a bone plate, the method comprising the steps of:
   (a) resecting the bone from a first side of the bone to a second side of the bone so as to leave a bony hinge on the second side;

(b) inserting an opening tool into the resection;

(c) opening the resection using the opening tool to a height at which the deformity is corrected;

(d) placing the bone plate in a location such that the bone plate spans the open resection;

(e) removing the opening tool; and (f) packing the resection with at least two individual pre-formed wedge shaped sections of material by inserting at least two individual pre-formed, unconnected wedge shaped sections into the open resection.

10. The method of claim 9, wherein the step of packing the resection includes the steps of inserting a smaller inner section of wedge shaped material behind the bone plate, and inserting two larger outer sections of wedge shaped material on either side of the smaller wedge section within the resection.

11. The method of claim 10, wherein the two wedge shaped sections of material have outer surfaces formed of cortical bone.

12. The method of claim 10, wherein the step of inserting the smaller inner section takes place prior to placing the bone plate.

13. The method of claim 9, wherein the material comprises allograft bone.

14. The method of claim 9, wherein the material comprises synthetic bone.

15. The method of claim 14, wherein the synthetic bone comprises a biodegradable polylactide combined with a hydroxyapatite or tricalcium phosphate.

16. The method of claim 9, further comprising the step of removing a removable handle from the opening tool after opening the resection and prior to placing the bone plate.

* * * * *